United States Patent [19]

Lynn et al.

[11] Patent Number: 5,447,495
[45] Date of Patent: Sep. 5, 1995

[54] APPARATUS AND METHODS FOR TRANSFERRING BLOOD BETWEEN A BLOOD ASPIRATOR ASSEMBLY AND AN EXTERNAL CONTAINER

[75] Inventors: Lawrence A. Lynn, 862 Curleys Ct., Worthington, Ohio 43085; James E. Cole, Ventura, Calif.

[73] Assignee: Lawrence A. Lynn, Columbus, Ohio

[21] Appl. No.: 266,747

[22] Filed: Jun. 28, 1994

Related U.S. Application Data

[63] Continuation-in-part of Ser. No. 540,605, Jun. 19, 1990, Pat. No. 5,114,400, which is a continuation of Ser. No. 760,468, Sep. 17, 1991, which is a continuation-in-part of Ser. No. 594,677, Oct. 10, 1990, Pat. No. 5,178,607, which is a continuation of Ser. No. 302,835, Jan. 27, 1989, which is a continuation-in-part of Ser. No. 80,406, Jul. 31, 1987, Pat. No. 4,838,855.

[51] Int. Cl.[6] .......................................... A61M 31/00
[52] U.S. Cl. ...................................... 604/49; 128/764
[58] Field of Search ............... 604/49, 52, 53, 201, 604/411, 414, 415, 4, 86–88; 128/760–765

[56] References Cited

U.S. PATENT DOCUMENTS

| | | |
|---|---|---|
| 2,357,238 | 8/1944 | Trimble . |
| 2,847,996 | 8/1958 | Cohen et al. . |
| 2,922,420 | 1/1960 | Cheng . |
| 3,067,742 | 12/1962 | Linke . |
| 3,344,785 | 10/1967 | Hamilton . |
| 3,406,685 | 10/1968 | May . |
| 3,986,508 | 10/1976 | Barrington . |
| 4,013,064 | 3/1977 | Patel . |
| 4,014,328 | 3/1977 | Cluff . |
| 4,022,205 | 5/1977 | Tenezar . |
| 4,051,852 | 10/1977 | Villari . |
| 4,058,121 | 11/1977 | Choksi . |
| 4,197,848 | 4/1980 | Garrett . |
| 4,214,779 | 7/1980 | Losell . |
| 4,219,021 | 8/1980 | Fink . |
| 4,276,880 | 7/1981 | Malim . |
| 4,335,717 | 6/1982 | Bujan . |
| 4,364,383 | 12/1982 | Vcelka . |
| 4,496,350 | 1/1985 | Cosentino . |
| 4,634,427 | 1/1987 | Hannula . |
| 4,645,491 | 2/1987 | Evans . |

(List continued on next page.)

FOREIGN PATENT DOCUMENTS

| | | |
|---|---|---|
| 0208975 | 1/1987 | European Pat. Off. . |
| 0367549 | 5/1990 | European Pat. Off. . |
| 2049513 | 3/1971 | France . |
| 9001349 | 2/1990 | WIPO . |
| WO9100115 | 6/1990 | WIPO . |
| 9011103 | 10/1990 | WIPO . |

OTHER PUBLICATIONS

Article, Burnum, Medical Vampires, May 8, 1986, pp. 1250–1251.

(List continued on next page.)

*Primary Examiner*—John D. Yasko
*Attorney, Agent, or Firm*—Cushman, Darby & Cushman

[57] ABSTRACT

An aspirator receiver forms part of a blood aspiration system for injecting fluid into a patient and withdrawing undiluted blood. The aspirator receiver has a housing with a passage occluded by a septum and in communication with the blood flow channel through the aspirator system. An aspirator comprises a cannula having a blunt tip surrounded by a shroud, the cannula being in communication with a blood receiving receptacle. The aspirator is applied to the housing with the shroud centering the cannula about and for penetration through the septum of the housing whereby undiluted blood may be withdrawn from the flow channel into the receptacle. Upon removal of the aspirator, the septum occluding the end of a standard vacuum-filled container is penetrated by the cannula whereby blood from the receptacle may be transferred into the container. The housing and container septa are of like external configuration and dimension and the shroud is complementary in dimension to facilitate transfer of the blood from the aspirator system to the receptacle and finally to the container.

12 Claims, 5 Drawing Sheets

U.S. PATENT DOCUMENTS

| | | |
|---|---|---|
| 4,650,468 | 3/1987 | Jennings . |
| 4,654,034 | 3/1987 | Masters . |
| 4,666,438 | 5/1987 | Raulerson . |
| 4,675,004 | 6/1987 | Hadford . |
| 4,675,005 | 6/1987 | De Luccia . |
| 4,675,007 | 6/1987 | Terry . |
| 4,677,017 | 6/1987 | Sato . |
| 4,699,612 | 10/1987 | Hamacher . |
| 4,710,180 | 12/1987 | Johnson . |
| 4,721,506 | 1/1988 | Teves . |
| 4,752,292 | 6/1988 | Lopez . |
| 4,759,756 | 7/1988 | Forman . |
| 4,763,648 | 8/1988 | Wyatt . |
| 4,776,843 | 10/1988 | Martinez . |
| 4,796,644 | 1/1989 | Polaschegg . |
| 4,799,494 | 1/1989 | Wang . |
| 4,834,152 | 5/1989 | Howson . |
| 4,834,716 | 5/1989 | Ogle, II . |
| 4,838,877 | 6/1989 | Massau . |
| 4,865,583 | 9/1989 | Tu . |
| 4,911,705 | 3/1990 | Heinzerling . |
| 4,920,970 | 5/1990 | Wyatt . |
| 4,935,010 | 6/1990 | Cox . |
| 4,981,140 | 1/1991 | Wyatt . |
| 4,981,469 | 1/1991 | Whitehouse . |
| 4,986,278 | 1/1991 | Ravid . |
| 4,998,927 | 3/1991 | Vaillencourt . |
| 5,135,489 | 8/1992 | Jepson . |
| 5,158,554 | 10/1992 | Jepson . |

OTHER PUBLICATIONS

Article, Walrath, Stopcock: Bacterial Contamination in Invasive Monitoring Systems Jan. 2, 1979, pp. 100–104.

Article, MacArthur et al, Stopcock Contamination in an ICU, Jan. 1975, pp. 96–97.

Article, Bourke, Errors in Intraoperative Hematocrit Determination Sep. 1976 pp. 357–359.

Article, Dennis et al, Effect of Sample Dilutions on Arterial Blood Gas Determination, Dec. 1985, pp. 1067–1068.

Catalog American Scientific Products, p. 1568, (1987–1988).

Brochure, Travenol Laboratories, Dialysis Products, (1984).

Article, Knox, Implantable Vascular Access Devices, pp. 70–73.

Article, Winters, Implantable Vascular Access Devices, Nov./Dec. 1984 pp. 25–30.

Article, Cannon, Arrington-Mitchell, & Fabian, Prospective . . . Heparinized Arterial Lines, Jul. 1985, pp. 392–395.

Article, Smoller, Kruskall, Phlebotomy for Diagnostic Laboratory Tests in Adults, May 8, 1986, pp. 1233–1235.

APPARATUS AND METHODS FOR TRANSFERRING BLOOD BETWEEN A BLOOD ASPIRATOR ASSEMBLY AND AN EXTERNAL CONTAINER

RELATED APPLICATIONS

This is a division of application Ser. No. 08/043,636, filed Apr. 1, 1993, now U.S. Pat. No. 5,324,256, which was a continuation of Ser. No. 07/760,468 filed Sep. 17, 1991, which is a continuation-in-part of application Ser. No. 07/594,677, filed Oct. 10, 1990, now U.S. Pat. No. 5,178,607, which is a continuation of application Ser. No. 07/302,835, filed Jan. 27, 1989 and, which in turn, is a continuation-in-part of application Ser. No. 80,406, filed Jul. 31, 1987, now U.S. Pat. No. 4,838,855. This application is also a continuation-in-part of U.S. patent application Ser. No. 07/540,605, filed Jun. 19, 1990, now U.S. Pat. No. 5,114,400. The disclosures of these applications are incorporated herein by reference as though fully set forth herein.

BACKGROUND AND SUMMARY OF THE INVENTION

In the above-noted U.S. Pat. No. 4,838,855 by one of the co-inventors hereof, there is disclosed an aspiration system for supplying fluid to and withdrawing undiluted blood from tubing connected to the blood vessel of a patient, for example, by an in-dwelling catheter, without opening the tubing system to atmosphere. In that system, a proximal section of tubing is placed in communication with a source of fluid under pressure, for example, intravenous fluid. The proximal tubing section extends to a two-way valve, which in turn is connected to an intermediate tubing section. The intermediate tubing section is connected to an aspirator receiver, in turn connected to distal tubing coupled to the in-dwelling catheter. In one position of the valve, the intermediate tubing section is connected with a fluid reservoir and in the other position of the valve, the intermediate tubing section is coupled with the source of fluid under pressure. The aspirator receiver includes a housing having a flow channel and a passage in communication with the flow channel and occluded by a septum. The septum is formed of resilient material such that a needle may penetrate the septum to withdraw blood from the flow channel and, upon withdrawal of the needle, the septum is self-sealing.

In that system, the fluid reservoir has a volume sufficient such that, when the valve is opened to afford communication between the reservoir and the intermediate and distal tubing sections and is closed to the source of fluid under pressure, sufficient resident fluid in those tubing sections can be withdrawn into the reservoir so that the aspirator receiver is filled with undiluted blood from the in-dwelling catheter through the distal tubing into the aspirator receiver flow channel. When the reservoir is full, a needle forming part of a syringe, may be inserted through the septum of the aspirator receiver and into communication with the blood in the flow channel. The undiluted blood under pressure thus fills the syringe. Once a satisfactory sample has been obtained, the syringe needle may be withdrawn from the aspirator receiver septum which automatically reseals. Pressure is then applied to the fluid temporarily resident in the reservoir to return such fluid to the tubing sections without loss of blood other than that actually removed for testing. Indeed, measurements can be made without any loss of blood by interfacing the blood analysis section directly with blood analysis sensors or membranes.

In our prior application Ser. No. 07/594,677, there are also disclosed certain improvements in the above-described system, including a blunt cannula or needle for use with a preperforated septum. As explained in that application, the use of a blunt cannula or needle prevents accidental needlesticks typically associated with inserting a needle through septa or, more generally, when using unprotected needles. The blunt needle is thus used in connection with a preperforated septum which is also self-sealing. The tip of the blunt needle enables the force required to pass the tip of the blunt needle into the septum to .be considerably less than the force required to penetrate the surface of normal intact human skin of the hand or arms whereby accidental misdirection of the blunt needle tip against the skin will not result in penetration of the skin. Hence, the risk of needlestick while obtaining blood sample through the septum is virtually eliminated.

In our application Ser. No. 07/540,605, filed Jun. 19, 1990, an improvement with respect to the two systems previously described is disclosed which eliminates the problem of blood spurting from the cannula tip when the cannula is removed from the septum of the aspirator receiver. The syringe typically has a bubble of air trapped within its interior chamber. The elevated pressure within the flow channel when the cannula is inserted through the septum positively pressurizes the syringe during sampling, compressing that air bubble. Upon removal of the cannula, the opening at the tip of the cannula is exposed to the lower atmospheric pressure, thus causing the pressurized air bubble within the syringe to expand and the blood to undesirably spurt from the tip of the cannula.

In application Ser. No. 07/540,605, that blood spurting problem is cured by enabling depressurization of the air bubble within the syringe while the cannula tip is occluded from fluid communication with the pressurized blood vessel. Although other means to occlude such fluid communication are included in the teaching, the preferred embodiment discloses the use of the septum to occlude the cannula near its tip. Particularly, a shroud is provided about the blunt cannula which, in cooperation with the aspirator receiver housing, indicates when the tip of the cannula is occluded within the septum during withdrawal of the cannula from the septum. Such occlusion indicator preferably includes cooperating detents on the aspirator receiver housing and the shroud affording sensory perception of the occlusion. When those detents engage, the sensory, e.g., tactile indication afforded thereby, permits the nurse to temporarily stop withdrawing the cannula from the aspirator receiver housing and to retract the syringe piston. This induces a negative pressure in the syringe barrel, enabling expansion of the trapped air bubble within the syringe. Upon full withdrawal of the cannula, the atmospheric pressure is at least equal to or greater than the pressure within the syringe thus eliminating the blood spurting problem.

Notwithstanding these various improvements in blood aspiration assemblies, there remains a significant problem in transferring the blood sample from the aforementioned syringe to another container, for example, the standard adult vacuum-filled container. A container of this type typically comprises a cylindrical glass or plastic tube closed at one end. Its opposite open end is normally occluded by a septum, i.e., a rubber stopper. Typically, a practitioner would penetrate the septum of the aspirator receiver with the needle of a conventional syringe, withdraw the needle once an adequate volume of blood had been withdrawn into the syringe, and then attempt to direct the needle tip for penetration through the septum of the vacuum container. Obviously, using that procedure, there is substantial danger of accidental needlestick during insertion of the needle of the syringe into the septum of the aspirator receiver, its withdrawal from that septum, movement of the syringe to the vacuum container, and attempted penetration of the rubber septum of the container.

Figures 10, 11:
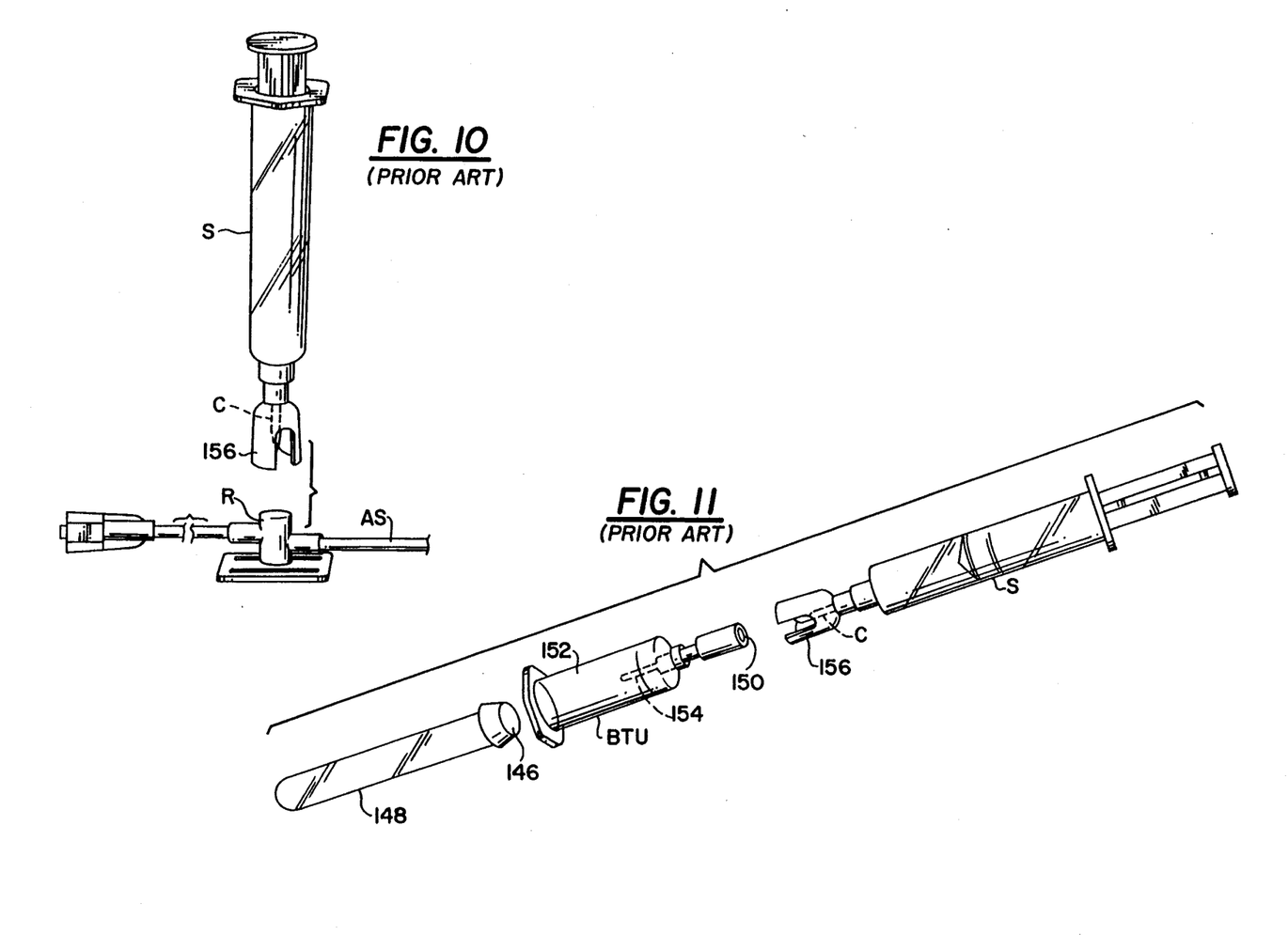
FIG. 10 is a perspective view of a portion of a prior art blood transfer apparatus illustrated as applied to an aspiration system.
FIG. 11 is a perspective view of the complete prior art blood transfer apparatus of FIG. 10 illustrating the successive transfer of blood from a syringe to a blood transfer unit and then to a vacuum-filled container.

This problem has been recognized and a very complex solution to the problem has been offered. Particularly, a blood protection system has been developed which is illustrated in FIGS. 10 and 11 hereof. That system includes a sampling syringe S (FIG. 6) having a shrouded cannula C. The shrouded cannula is applied to the septum of an aspirator receiver R of an aspiration system AS to withdraw a blood sample. The cannula C is then removed from the aspirator receiver housing. The cannula, however, is too blunt to penetrate the septum 146, usually formed of rubber or like material, of the vacuum-filled container 148 to effect direct transfer of the blood sample to the container. Moreover, the shroud about the cannula does not match the septum on the standard adult vacuum-filled container C (FIG. 11). This system thus employs an intermediate blood transfer unit BTU which includes a bore at one end occluded by a septum 150 penetrable by the shrouded blunt cannula C. At the opposite end, there is provided an elongated cylindrical chamber 152 open at one end for receiving the vacuum-filled container C, septum end first. The container is advanced within this chamber such that a needle 154 forming part of the blood transfer unit may penetrate the septum of the vacuum container 148. The needle 154 is in communication with the bore at the opposite end of the blood transfer unit. When the container 148 and sampling syringe S are connected to the blood transfer unit, blood is then transferred from the sampling syringe S through its blunt cannula C, and through the septum 150 and bore at one end of the blood transfer unit BTU and then through the needle 154 of the blood transfer unit through the septum of the vacuum container for reception within the container. Direct transfer of blood from the sampling syringe S to the container 148 in that system is not possible because the blunt cannula C is not sufficiently sharp to penetrate the septum 146 of the vacuum-filled container 148. Also, the shroud 156 of the sampling syringe is too small to accommodate the septum of the vacuum-filled container.

According to the present invention, there is provided apparatus and methods for transferring blood between the aspirator receiver of a blood aspiration system and a standard adult vacuum-filled container which minimizes problems associated with needlesticks and consequent transmittal of infectious diseases and the need for any intermediate blood transfer unit. In accordance with the present invention, there is provided an aspirator having at one end a cannula extending within, but radially spaced from, a surrounding shroud. The tip of the cannula is blunt yet sufficiently sharp to penetrate the septum of a standard vacuum-filled container. Direct transfer of the blood sample from the aspirator to the vacuum container is accomplished by (i) forming the septum of the aspirator receiver housing (including any surrounding portion of the housing) substantially identical in shape and dimension to the septum of the standard adult vacuum-filled container; and (ii) forming the interior of the shroud complementary to both the septum of the aspirator receiver housing (including any surrounding portion of the housing) and the septum of the standard adult vacuum-filled container. Further, the shroud extends distally beyond the tip of the cannula. While thus recessed from the end of the shroud, the cannula is exposed to engagement by an individual's finger inserted within the open end of the shroud because the interior diameter required to receive an adult vacutainer is larger than the adult human finger. The tip of the cannula is therefore formed sufficiently blunt to prevent penetration of intact human skin on an individual's hands and arms even upon application of casual inadvertent force.

To facilitate the transfer of the blood sample from the aspiration system to the vacuum-filled container, the aspirator includes an interior chamber or receptacle in communication with the bore of the cannula for receiving blood from the flow channel of the aspirator receiver through the cannula. The interior chamber can include a plunger for displacing the blood sample into the vacuum-filled container when the aspirator and container are connected.

Preferably, the end of the aspirator receiver housing having the passage occluded by the septum is substantially identical in shape and dimension to the end of the vacuum-filled container including its septum. Particularly, the aspirator receiver housing and vacuum-filled container ends are preferably cylindrical, similar or identical in diameter and complementary in diameter to the internal diameter of the preferably cylindrically-shaped shroud surrounding the cannula. In this manner, the aspirator may be centered over the septum of the aspirator receiver housing by engagement of the shroud about the housing end or septum to enable substantial coaxial penetration of the septum, preferably through a perforation in the septum. Penetration may therefore proceed without danger of breaking the cannula by canting it relative to the housing. Upon receipt of the blood sample within its interior chamber, the aspirator may be withdrawn from the aspirator receiver housing, preferably using the aspirator occlusion indicator of the previously mentioned application, to avoid the problem of blood spurting from the cannula tip upon complete removal of the aspirator. Once removed, the aspirator may be similarly centered upon the stopper of the vacuum-filled container by engagement of the shroud about the stopper. The blunt cannula is sufficiently sharp to penetrate the stopper of the vacuum-filled container without preperforating the septum. The plunger of the aspirator may then be actuated to facilitate displacement of the blood sample from the aspirator directly into the container. Upon separation of the aspirator and container, the stopper of the vacuum-filled container automatically seals.

In a preferred embodiment according to the present invention, there is provided, in combination with a blood aspiration system connected to a pressure transducer and a discrete container, an apparatus for transferring a sample of blood from the aspiration system to the discrete container comprising an aspirator including an axially extending cannula having a distal tip, the cannula having a bore with first and second openings adjacent opposite ends of the bore and a shroud extending about the cannula in transversely spaced relation thereto, the shroud extending axially beyond the distal tip of the cannula, an aspiration receiver which forms part of the blood aspiration system and which includes a housing having a flow channel for communication with the human vasculature for flowing blood through the flow channel, the housing having a portion for receiving the cannula to locate the first opening of the cannula in communication with the flow channel. Blood receiving means are coupled to the aspirator in communication with the second opening for receiving blood. The discrete container has an opening at one end and a stopper occluding the opening, the external configurations of the one end of the container and the housing receiving portion, respectively, being complementary to the internal configuration of the shroud whereby, (i) upon application of the aspirator to the aspirator receiver, the shroud engages about the housing receiving portion and centers the cannula for penetration of the housing receiving portion to locate the first opening in communication with the flow channel and thereby to communicate blood from the flow channel through the bore into the blood receiving means, and, (ii) upon removal of the aspirator from the aspirator receiver and upon application of the aspirator to the container, the shroud engages about the container end and centers the cannula for penetration through the septum of the container to locate the first opening in communication with the container and thereby to communicate blood from the receiving means through the bore into the container.

In a further preferred embodiment according to the present invention, there is provided apparatus for transferring a sample of blood from a flow channel in fluid communication with an aspirator receiver to a discrete container closed at one end by a stopper, the flow channel being adapted for communication with the lumen of a blood vessel of a patient and a passage of the aspirator receiver opening through an aspirator receiver portion having a predetermined outside diameter and which passage is occluded by a septum, comprising an aspirator including an axially extending cannula having a distal tip, a first opening adjacent the tip for receiving blood from the flow channel upon penetration of the septum by the cannula, a second opening and a bore through the cannula extending between the first and second openings, the cannula being adapted for connection to a receptacle for communicating blood received through the first opening into the bore and through the second opening into the receptacle and a generally cylindrical shroud extending about the cannula in radially spaced relation thereto and extending distally axially beyond the distal tip of the cannula, the internal diameter of the shroud being at least as great as about 17.5 mm for successively receiving the aspirator receiver portion and the ends of the container enabling transfer of blood directly from the aspirator receiver to the receptacle and from the receptacle directly through the cannula to the container.

In a further preferred embodiment according to the present invention, there is provided a method of transferring a sample of blood from a flow channel in an aspirator receiver of an aspiration system to a discrete container having a septum closing one end thereof wherein the flow channel is adapted for communication with the lumen of a blood vessel of a patient and the aspirator receiver has a housing portion for receiving a cannula, comprising the steps of providing a flow of blood from the patient into the flow channel, positively centering the cannula of the aspirator relative to the housing receiving portion by engaging a shroud on the aspirator about the housing receiving portion, penetrating the housing receiving portion with the centered cannula to place the cannula in communication with the blood in the flow channel, flowing blood from the flow channel through the cannula for reception in a receptacle in communication with the cannula, removing the aspirator from the aspirator receiver, positively centering the cannula relative to the septum of the container by engaging the shroud of the aspirator about the end of the container, penetrating the septum of the container with the centered cannula to place the container in communication with the blood in the receptacle and flowing blood from the receptacle into the container.

It is therefore a primary object of the present invention to provide apparatus and methods for the direct transfer of a blood sample from a blood aspirator assembly to an adult vacuum-filled container without injury from needlesticks, in a manner achieving a centering of the cannula relative to the septa thereby avoiding breaking the cannula, and without the need for any intermediate blood transfer unit.

These and further objects and advantages of the present invention will become more apparent upon reference to the following specification, appended claims and drawings.

DETAILED DESCRIPTION OF THE DRAWING FIGURES

Reference will now be made in detail to a present preferred embodiment of the invention, an example of which is illustrated in the accompanying drawings.

Figure 1:
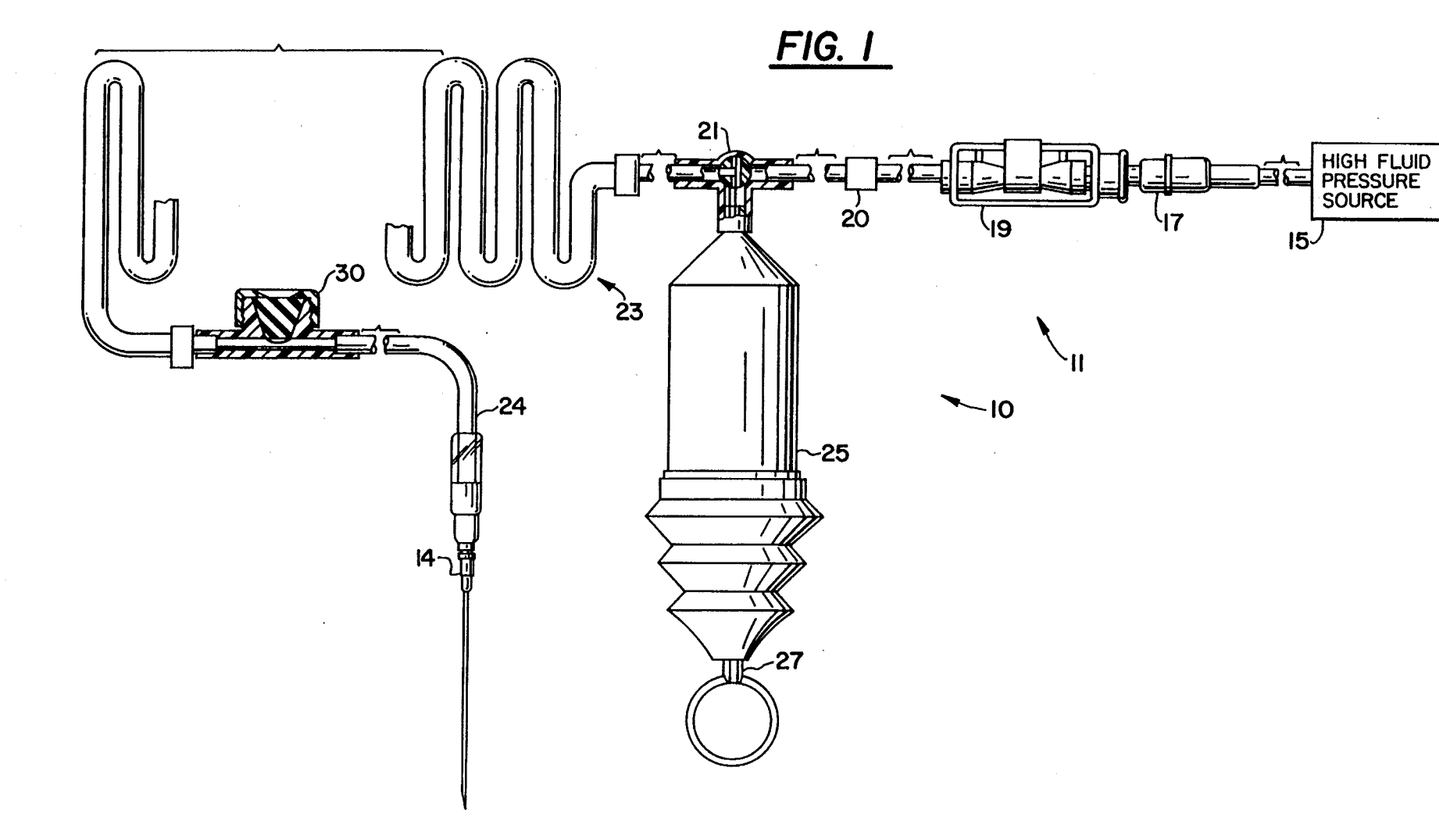
FIG. 1 is a fragmentary schematic illustration with portions in cross section of a blood aspiration system employing apparatus and methods for transferring blood from the system to an external container according to the present invention.

Referring now to the drawings, particularly to FIG. 1, there is illustrated a blood aspiration system of the type disclosed in our prior co-pending application Ser. No. 07/302,835, filed Jan. 27, 1989, and which includes tubing, generally indicated 10, having proximal and distal end tubing sections 11 and 24, respectively. A fluid source 15 under pressure, for example, an intravenous fluid-filled pressure bag, is in communication with proximal tubing section 11. Tubing section 11 is connected to a conventional coupling 17 for a conventional trigger squeeze one-way valve mechanism 19. The distal end of valve mechanism 19 is coupled to a pressure transducer 20, in turn connected to a two-way valve 21. Pressure transducer 20 is per se conventional and is typically used to monitor blood pressure. Valve 21 is coupled to an intermediate tubing section 23, for purposes described hereinafter. Valve 21 has a port in communication with a fluid reservoir 25 having a manually-operated piston 27. Valve 21 may be manually operated to provide (i) communication between fluid source 15 and intermediate tube 23 through tubing section 11, thereby preventing communication between tubing 10 and reservoir 25; or (ii) communication between tubing section 23 and reservoir 25, thereby preventing communication between reservoir 25 and tubing section 11 with the fluid source 15.

Tubing section 23 preferably comprises a generally larger diameter tube than tubing 24 for reasons discussed hereinafter, and has its distal end coupled to a blood aspirator receiver 30 forming part of the present invention. Blood aspirator receiver 30 is in turn coupled to tubing section 24 connected to a catheter 14.

From a review of the foregoing description and prior application Ser. No. 07/302,835, it will be appreciated that intravenous fluid from fluid source 15 fills tubing 10 and the various elements between the source and the catheter excluding reservoir 25 whereby fluid is administered to the patient. To withdraw a blood sample from the patient, valve 21 is manipulated to place reservoir 25 in communication with the tubing 23 and, hence, the vasculature system of the patient through distal tubing end section 24 and catheter 14. By withdrawing piston 27 of reservoir 25, a predesignated volume of fluid resident in tubing sections 23 and 24 is withdrawn into reservoir 25. This enables a fluid volume to be withdrawn into the enlarged tubing section 23 which is not sufficient to permit blood from the patient's vasculature to enter reservoir 25, but sufficient to provide blood in the aspirator receiver 30 which is substantially undiluted by the resident intravenous fluid. The fluid connection between the aspirator receiver 30 and the reservoir 25 is then occluded. A blood sample is then withdrawn from the aspirator receiver housing 30 by penetrating its septum with the blunt cannula of an aspirator to be described. The blood sample is then transferred from the aspirator of the blood transfer apparatus hereof to the container. After a blood sample is taken, the fluid communication between the aspirator receiver 30 and the reservoir 25 is reopened and the piston 27 in reservoir 25 is advanced to discharge the fluid temporarily stored therein into the tubing to return blood within the tubing to the patient. Once reservoir 25 is emptied, valve 21 is rotated to provide communication between fluid source 15 and catheter 14 whereby intravenous fluids can be further administered to the patient and to flush any residual blood from the system.

Figures 2, 3:
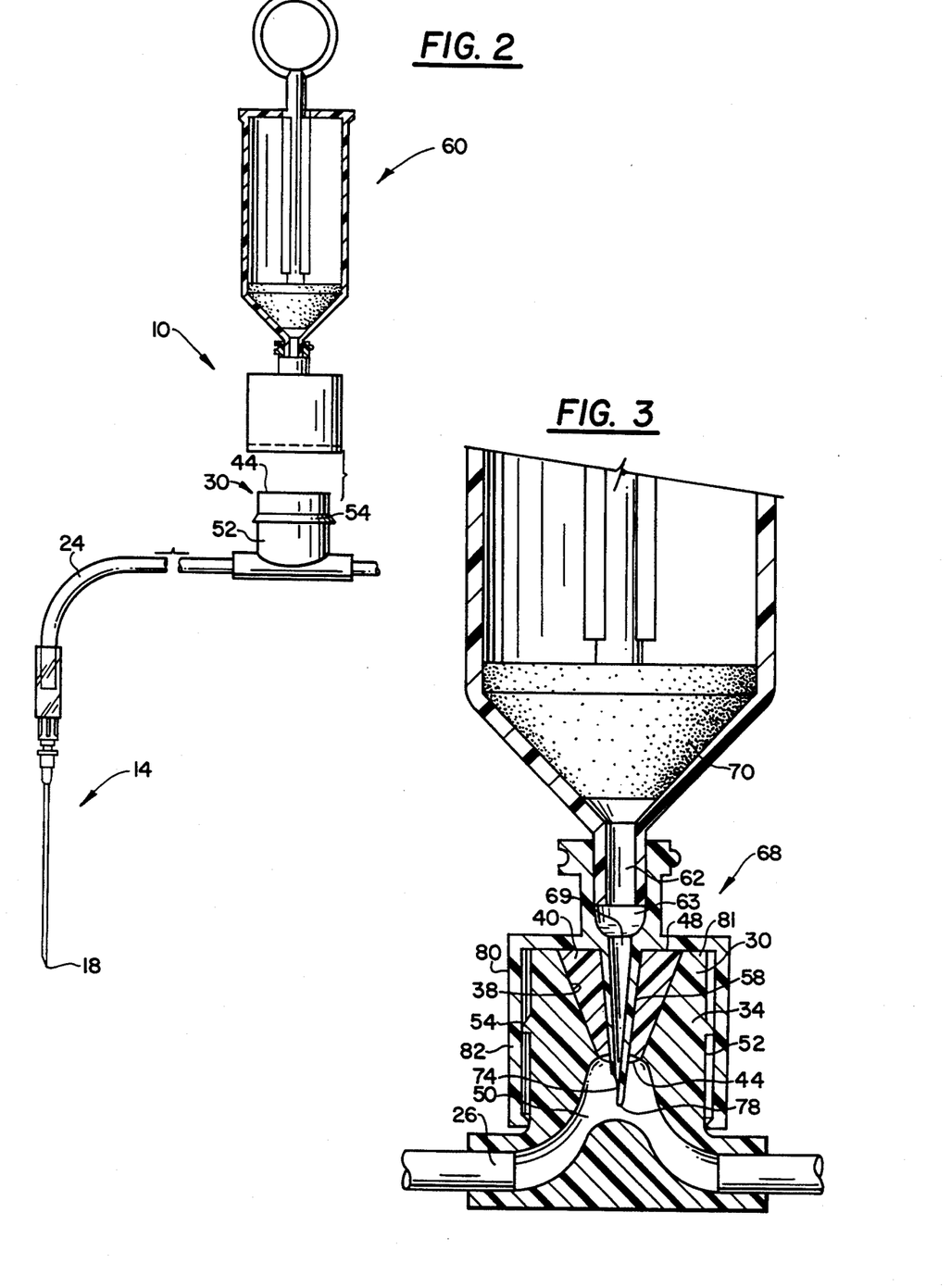
FIG. 2 is a side elevational view with parts broken out and in cross-section illustrating a portion of the aspiration system including the blood transfer apparatus according to the present invention.
FIG. 3 is an enlarged fragmentary cross-sectional view illustrating the blood transfer apparatus hereof connected to the septum of an aspirator receiver of the aspiration system.

Referring to the form of the aspirator receiver 30 illustrated in FIG. 3, aspirator receiver 30 includes a housing 34 having a flow channel 50 and a passage 38 in communication with flow channel 50. Passage 38 is occluded by an elongated elastomeric septum 40 which extends from a flow channel interface 44 to an atmospheric interface 48. A central perforation extends from the atmospheric interface 48 of septum 40 to the flow channel interface 44. The outer surface 52 of housing 34 preferably has an annular housing detent 54. Housing 34 may be formed of a rigid plastic material or may be formed of an elastomeric material harder than the elastomeric material of septum 40 or may itself comprise septum 40. Alternative embodiments of septa are also disclosed in our prior application Ser. No. 07/302,835.

The blood transfer apparatus hereof further includes an aspirator 68 and a receptacle for receiving the blood Sample withdrawn from flow passage 50. The receptacle may comprise the barrel of a conventional syringe 60. Syringe 60 includes a syringe tip 62 which lies in communication with the bore 63 of an elongated hub 68. Adjacent the distal end of hub 68, there is provided a cannula 58 having a bore 69 in communication with the bore 63 of hub 68. Cannula 58 terminates in a blunt tip 78, described in detail hereafter, having a side opening 74 which, when the aspirator is applied to the aspirator receiver 30 lies in communication with flow channel 50. Thus, a flow passage is established between flow channel 50 and the receptacle or the barrel of syringe 60 through the communicating bores 69, 63 and 62. A piston or plunger 70 is mounted within the receptacle or barrel of syringe 60.

Figure 4:
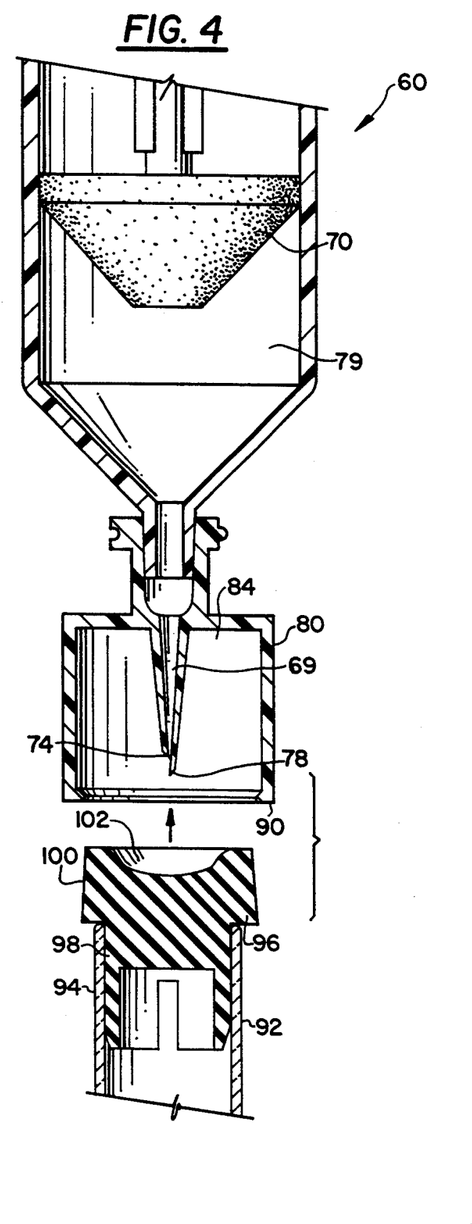
FIG. 4 is an enlarged view similar to FIG. 3 illustrating the blood transfer apparatus hereof poised for centering on the septum of an adult vacuum-filled container.
Figure 5:
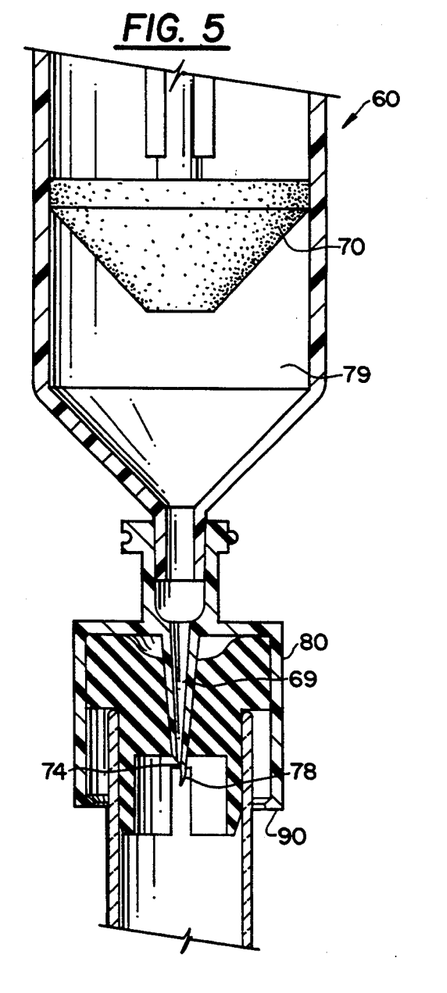
FIG. 5 is a view similar to FIG. 4 illustrating the blood transfer apparatus applied to the container in position to transfer blood from the blood transfer apparatus to the container.

Preferably forming an integral part of the aspirator is a shroud 80, which includes a base 81 extending radially outwardly from and adjacent one end of cannula 58. Shroud 80 also includes an enclosure, preferably a generally-cylindrical skirt 82, depending from base 81. The internal surface 86 of skirt 82 is complementary to the outer surface of aspirator receiver housing 34. Particularly, the internal configuration and dimension of shroud 80, defined by the internal surface 86 of skirt 82, is substantially complementary and equal to the external configuration and dimension of the outer surface 52 of the aspirator receiver housing 34. The spacing between housing 34 and skirt 82 is exaggerated in FIG. 3 to illustrate the detenting action forming part of the aspirator occlusion indicator described below. The distal end of shroud 80 also terminates in an inwardly extending detent 90 (FIGS. 4 and 5).

When employing the aspirator, the shroud is initially centered upon aspirator receiver housing 34, thereby centering the tip 78 of cannula 58 in the preperforated septum 40. By displacing the aspirator axially toward the aspirator housing, shroud detent 90 is pushed past housing detent 54 as the cannula tip is advanced through the preperforated septum 40. Upon full penetration, the cannula tip lies within flow channel 50 enabling a blood sample to be withdrawn through cannula tip opening 74 and bores 69, 63 and 62 into the barrel of the syringe. In the final position of assembly of the aspirator on the aspirator receiver housing, note that detents 54 and 90 are spaced axially one from the other. When sampling is completed, the aspirator is withdrawn axially from the aspirator receiver housing.

However, during withdrawal, shroud detent 90 engages housing detent 54 to provide a tactile indication that the cannula tip opening 74 is occluded by the elastomeric septum 40. At that point, the chamber 79 of the receptacle or syringe barrel is completely sealed so that withdrawal of piston 70 cannot draw air or additional blood into the receptacle or syringe 60, but rather, will eliminate any positive pressure within chamber 79. That is, any air bubble extant in chamber 79, upon slight withdrawal of the piston of the syringe, will obtain atmospheric or negative pressure rather than its previous positive pressure. Thus, upon further withdrawal of the aspirator from the aspirator receiver housing, i.e., the cannula 58 from septum 40, the air entrapped within the syringe barrel, being at a pressure equal to or lower than atmospheric pressure, will preclude blood from spurting from the cannula tip upon its removal from the aspirator receiver housing. It will be appreciated that other types of sensory indications may be provided for indicating when the cannula tip is sealed. For example, gradations on the housing, colored or clear, or bayonet type joints between the aspirator and housing may be employed.

Once the aspirator has been removed from the aspirator receiver housing, it is applied and connected directly to a standard adult vacuum-filled container to transfer the blood sample from the chamber 79 into the container. With reference to FIGS. 4 and 5, a standard adult vacuum-filled container 92 comprises a cylindrical, typically glass or plastic, housing 94 closed at one end and open at its opposite end. The open end is normally occluded by a septum 96, e.g., a rubber stopper. Septum 96 has a neck portion 98 received in the open end of container 94 and a radially outwardly directed flange 100 overlying the end of container 92, the outer face of septum 96 being conventionally recessed at 102. Septum 96 is not preperforated and the rubber material forming septum 96 must be slit or perforated by the cannula 58 of the blood transfer apparatus in order to locate cannula tip 78 within container 94 and tip opening 74 in communication with the container, as illustrated in FIG. 5. The dimensions and forces necessary to accomplish this are set forth below in terms of the bluntness of the needle and the force required to penetrate the septum.

In accordance with the present invention, the internal surface 86 of shroud 80 is complementary to the external surface about the septum 96 of the container 92. Particularly, the internal configuration and dimension of shroud 80 is substantially complementary to the external diameter dimension and configuration of the septum 96. Thus, the shroud is complementary to both the aspirator receiver housing and the septum of the container.

To transfer the blood sample into container 92, the aspirator and container are aligned such that shroud 80 is in substantial axial alignment with septum 96. By forming shroud 80 complementary to septum 96, particularly the flange 100 of the septum 96, shroud 80 and, hence cannula 58, may be centered with respect to septum 96. Thus, when the aspirator and septum of the container are connected, the septum is received within the shroud with the shroud centering and coaxially aligning the cannula relative to the septum and the container. That is, a substantially coaxial relation is obtained between the container and the cannula such that by engaging the shroud and septum, the cannula cannot substantially cant or incline upon application of the force necessary for the cannula to penetrate the septum. This prevents the cannula from being broken or fractured upon penetration through the septum.

To effect transfer of the blood sample from the aspirator directly to the adult vacuum-filled container in accordance with the present invention the external configurations of the aspirator receiver housing and the occluded end of the vacuum-filled container are substantially identical in configuration and dimension relative to one another and complementary to the internal configuration and dimension of the shroud. Preferably, these configurations are generally cylindrical and therefore the diameters of the aspirator receiver housing and the septum of the vacuum-filled container are substantially equal enabling these elements to form a relatively close or tight fit with the shroud, whose internal diameter is therefore only slightly larger. By applying an axial force to the aspirator, the cannula penetrates through septum 96 of the vacuum-filled container until the base of the shroud engages the outer surface of the septum. At that time, opening 74 at the distal end of the cannula is located beyond the septum and within the container. The piston of the syringe may then be advanced to displace the blood sample from the syringe into the container. When the container is filled sufficiently, the cannula is withdrawn and the elastomeric material the septum 96 seals the opening.

In the preferred form hereof, the septum or stopper 96 is generally cylindrical and has a diameter of about 16 mm. The internal diameter of the shroud is about 17.5 mm. The diameter of the aspirator receiver housing portion which receives the shroud and includes the septum receiving cannula has an outer diameter of about 17.5 mm. The length of the aspirator receiver housing from the face of its septum to the bottom of the housing is 18 mm. With respect to septa 40 or 96, each septum per se may extend to the full diameter indicated or be surrounded by another part or housing which has that diameter of. It is significant, however, that the diameters of the septa be substantially equal to one another and that the internal diameter of the shroud be sufficiently large to accommodate both septa. It will also be appreciated that there is a small population of vacuum-filled containers having septa with diameters smaller than noted above. These likewise may be used with the direct blood transfer apparatus hereof as they too are sized for reception within the shroud.

In accordance with another aspect of the present invention, cannula 58 has a blunt tip sufficiently sharp to penetrate the otherwise unpenetrated, unperforated septum of the vacuum-filled container yet not sufficiently sharp with casual force to penetrate an individual's skin whereby the problem of inadvertent needlestick is greatly reduced. It will be appreciated that because the aspirator receiver housing and septum of the vacuum-filled container have substantial diameters, and notwithstanding that the shroud extends axially beyond the distal tip of the cannula, there is a sufficient opening at the distal end of the shroud for the finger of an individual to touch the tip of the cannula, hence, the potential for a needlestick injury. To prevent that, as well as to afford the cannula sufficient sharpness to penetrate the closed septum of the vacuum-filled container, the blunt tip of the cannula is formed particularly to achieve those objectives.

Figure 6:
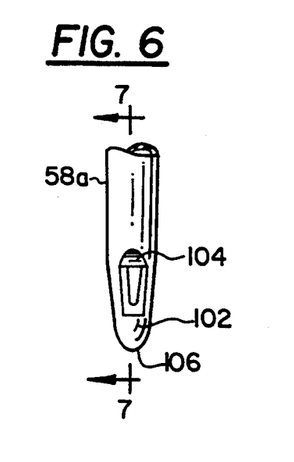
FIGS. 6 and 8 are fragmentary side elevational views of the tips of respective embodiments of two cannulas forming part of the present invention.
Figure 7:
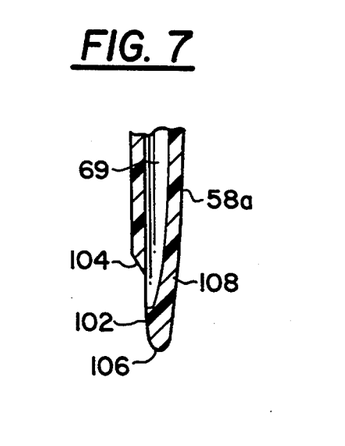
FIGS. 7 and 9 are cross-sectional views thereof taken generally about on lines 7—7 and 9—9 of FIGS. 6 and 8, respectively.

Referring to FIGS. 6 and 7, cannula 58 has a rounded tip 100. The radius of curvature of tip 100 is about 0.25 mm, for use with the perforated septum 40. With particular reference to FIG. 7, one side 102 of cannula 58a near tip 100 is recessed at 102.

The hub 68 of the aspirator has a longitudinal bore 63 of low internal volume which is in open communication with bore 69 of cannula 58a. Bore 69 tapers from a larger diameter to a smaller diameter as it extends distally. Near the distal end of cannula 58a, bore 69 angles at approximately 20° toward the recessed side 102 and has the opening 74 through side 102. To the proximal side of opening 74, cannula 58a has a smooth slanted edge 104.

Beyond the rounded tip 100, as the cannula 58a extends proximally, it can flare out into a conical section 106 having an angle of about 30°, as shown in FIG. 7. Thence, the needle extends into a conical section 108 having a smaller angle than 30°, such as an angle of about 20°, also as shown on the right of FIG. 7.

With a form of septum 40 of the type described in FIGS. 18-20 of our co-pending application Ser. No. 07/302,832, to achieve total penetration of septum 40 by a polycarbonate cannula 58a having dimensions heretofore described to position the tip 100 within the flow channel 50, as illustrated in FIG. 3, the aspirator can be applied to and inserted into the septum by a force of about 4.1 pounds ($1.824 \times 10^6$ dynes) applied perpendicular to the surface of the septum. Additionally, the force required for the aspirator to penetrate the stopper of a conventional vacutainer is about 5.4 pounds ($2.402 \times 10^6$ dynes). As known, a sharp 20-gauge steel needle of the type conventionally used in the prior art results in penetration of the skin of the dorsum of the hand with a force of about 0.12 pounds (53,376 dynes).

A cannula 58 having a tip with a radius of curvature of 0.20 mm to about 1 mm can also be used with the septa previously described.

Figure 8:
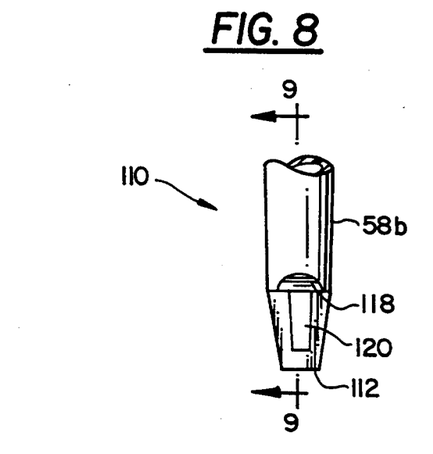
Figure 9:
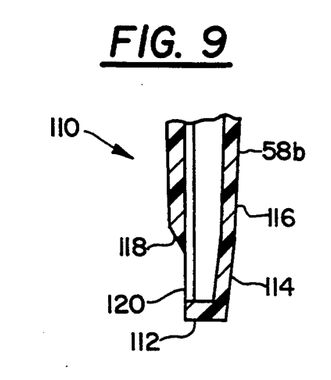

FIGS. 8 and 9 show a modified cannula 58b having a modified tip 110. The end 112 of tip 110 is flat, and, in an embodiment, can have a diameter of 1.0 mm. The tip angle at 114 can be about 15° and can extend proximally into a section 116 having a smaller angle of about 10°, as seen viewing FIG. 9 toward the right side. The flat end surface 112 can have an area of 0.78 square mm which can be of circular shape. One side of the distal end of cannula 58b is recessed at 118 and has an opening 120 extending therethrough in flow communication with bore 69.

While the foregoing specifically notes the application of the aspirator to a standard size adult vacutainer, it will be appreciated that the present invention also embraces other sizes of vacutainers. For example, pediatric vacutainers of smaller dimensions, e.g., diameter, are frequently employed with blood transfer apparatus. In those situations, the aspirator receiver is sized complementary to the aspirator and the aspirator is similarly sized complementary to the pediatric vacutainer.

In contrast with the aforementioned easy penetration of the skin achieved by the typical steel needle, cannula 58b with tip 110 of FIGS. 8 and 9 fails to penetrate the skin of the dorsum of the hand when directed against it at a force of 2.3 pounds (1,023,040 dynes). Hence, it too is much less likely than the conventional steel needle to penetrate the human skin accidentally when the cannula 58b contacts the skin through casual contact.

In summary, the present invention provides a balance between the necessity of providing a cannula having a tip sufficiently blunt to avoid accidental needlestick injury upon application of the finger to the tip of the needle with casual force and sufficiently sharp to afford penetration of the standard septum of a vacutainer. This balance of the degree of bluntness of the tip of the cannula is necessary because the shroud about the cannula must be sufficiently large to receive the end of the vacutainer carrying the septum, which also means that the shroud is sufficiently large to receive the end of a human finger.

Tests have demonstrated that the force required to insert into and extract the cannula from the septum constructed as previously described are as follows:

Insertion Force—4.1 pounds or $1.824 \times 10^6$ dynes
Extraction Force—7.5 pounds or $3.336 \times 10^6$ dynes Tests have also demonstrated that the required force necessary to penetrate the stopper or septum of a vacutainer with the aforedescribed cannula is as follows:

Penetration Force—5.4 pounds or $2.402 \times 10^6$ dynes

Additionally, the shroud centers the cannula about the septum and stopper facilitating insertion and substantially prevents the cannula from canting or tilting relative to the septum and stopper, precluding or minimizing the potential for breaking of the cannula.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for transferring blood from a tubing system in fluid connection with a patient's blood vessel into a discrete evacuated container having a closed penetrable first end, said tubing system having a flow channel capable of being filled with blood from said blood vessel and said tubing system further carrying a receiver in fluid communication with said flow channel, the method comprising steps of:
  a. providing a cannula for insertion into said receiver, said cannula carrying an adapter sized to be received over said receiver for guiding said cannula into said receiver, said cannula having an open first end for connection to a syringe and an open second end for insertion into said receiver;
  b. connecting said cannula to said syringe;
  c. inserting said cannula into said receiver by passing said adapter over said receiver until said second end of said cannula is in fluid communication with said flow channel;
  d. withdrawing a sample of blood through said cannula into said syringe;
  e. removing said cannula and said adapter away from said receiver;
  f. positioning said cannula and said adapter adjacent said closed penetrable first end of said evacuated container;
  g. advancing said cannula and said adapter relative to said evacuated container so that said adapter advances over said evacuating container until said cannula penetrates said closed container end;
  h. flowing blood from said syringe into said evacuated container.

2. A method for transferring blood from a tubing system in fluid connection with a patient's blood vessel into a discrete evacuated container having a closed penetrable first end, said tubing system having a flow channel capable of being filled with blood from said blood vessel and said tubing system further carrying a receiver having a guide, said receiver being in fluid communication with said flow channel, the method comprising steps of:
  a. providing a cannula for insertion into said receiver, said cannula carrying a adapter sized to be received over said guide for guiding said cannula into said receiver, said cannula having an open first end for connection to a syringe and an open second end for insertion into said receiver;
  b. connecting said cannula to said syringe;
  c. inserting said cannula into said receiver by passing said adapter over said guide until said second end of said cannula is in fluid communication with said flow channel;
  d. withdrawing a sample of blood through said cannula into said syringe;
  e. removing said cannula and said adapter away from said receiver;
  f. positioning said cannula and said adapter adjacent said closed penetrable first end of said evacuated container;
  g. advancing said cannula and said adapter relative to said evacuated container so that said adapter advances over said evacuating container until said cannula penetrates said closed container end;
  h. flowing blood from said syringe into said evacuated container.

3. A method as in claim 1, wherein said step of providing a cannula comprises providing a cannula carrying an adapter including a shroud sized to be received over said receiver and to selectively be received over said closed penetrable first end of said evacuated container.

4. A method as in claim 3, wherein said step of inserting said cannula by passing said adaptor over said receiver comprises telescopingly receiving said receiver in said shroud.

5. A method as in claim 1, wherein said step of providing a cannula carrying an adapter comprises providing a cannula carrying an adaptor having a shroud that extends axially beyond the second end of the cannula.

6. A method as in claim 3, wherein said step of advancing said cannula and said adaptor relative to said evacuated container comprises telescopingly receiving said evacuated container in said shroud so that said cannula penetrates said closed container end.

7. A method as in claim 2, wherein said guide comprises an exterior configuration of said receiver and said step of inserting said cannula into said receiver comprises passing said adaptor over said exterior configuration of said receiver.

8. A method as in claim 2, wherein said step of providing a cannula comprises providing a cannula carrying an adapter including a shroud sized to be received over said receiver and to selectively be received over said closed penetrable first end of said evacuated container.

9. A method as in claim 8, wherein said guide has a cross-sectional configuration generally corresponding to an internal configuration of said shroud of said adapter.

10. A method as in claim 8, wherein said step of inserting said cannula by passing said adaptor over said guide comprises telescopingly receiving said guide in said shroud.

11. A method as in claim 2, wherein said step of providing a cannula carrying an adapter comprises providing a cannula carrying an adaptor having a shroud that extends axially beyond the second end of the cannula.

12. A method as in claim 8, wherein said step of advancing said cannula and said adaptor relative to said evacuated container comprises telescopingly receiving said evacuated container in said shroud so that said cannula penetrates said closed container end.

* * * * *